US010849858B2

(12) United States Patent
Mambrini et al.

(10) Patent No.: US 10,849,858 B2
(45) Date of Patent: Dec. 1, 2020

(54) PROCESS FOR THE PREPARATION OF ERYTHROCYTES LOADED WITH ONE OR MORE SUBSTANCES OF PHARMACEUTICAL INTEREST AND SO OBTAINED ERYTHROCYTES

(71) Applicant: ERYDEL S.P.A., Urbino (IT)

(72) Inventors: Giovanni Mambrini, Mirandola (IT); Luca Benatti, Monza (IT); Giovanni Capogrossi, Jesi (IT); Marco Mandolini, Senigallia (IT)

(73) Assignee: ERYDEL S.P.A., Urbino PU (IT)

( * ) Notice: Subject to any disclaimer, the term of this patent is extended or adjusted under 35 U.S.C. 154(b) by 477 days.

(21) Appl. No.: 14/888,486

(22) PCT Filed: May 9, 2014

(86) PCT No.: PCT/IB2014/061338
§ 371 (c)(1),
(2) Date: Nov. 2, 2015

(87) PCT Pub. No.: WO2014/181309
PCT Pub. Date: Nov. 13, 2014

(65) Prior Publication Data
US 2016/0051482 A1 Feb. 25, 2016

(30) Foreign Application Priority Data

May 10, 2013 (IT) .............................. RM2013A0280
Nov. 5, 2013 (IT) .............................. RM2013A0610

(51) Int. Cl.
*A61K 9/50* (2006.01)
*A61K 35/18* (2015.01)
*A61K 31/661* (2006.01)
*A61K 38/45* (2006.01)
*C12N 5/078* (2010.01)

(52) U.S. Cl.
CPC .......... *A61K 9/5068* (2013.01); *A61K 9/5089* (2013.01); *A61K 31/661* (2013.01); *A61K 35/18* (2013.01); *A61K 38/45* (2013.01); *C12N 5/0641* (2013.01); *C12Y 207/01001* (2013.01)

(58) Field of Classification Search
None
See application file for complete search history.

(56) References Cited

U.S. PATENT DOCUMENTS

| 4,327,710 | A | 5/1982 | DeLoach et al. |
| 6,139,836 | A | 10/2000 | Magnani et al. |
| 9,089,640 | B2 | 7/2015 | Mambrini et al. |
| 2013/0101463 | A1 | 4/2013 | Mambrini et al. |

FOREIGN PATENT DOCUMENTS

| EP | 0 882 448 | 12/1998 |
| WO | 2011/135429 | 11/2011 |
| WO | 2011/135431 | 11/2011 |

OTHER PUBLICATIONS

Guest et al., Osmometric Behavior of Normal Human Erythrocytes, J Clin Invest. 1942; 21 (3): 257-262.*
Antonelli et al., New Strategies to Prolong the In Vivo Life Span of Iron-Based Contrast Agents for MRI, PLOS ONE, Oct. 2013, vol. 8, Issue 10, e78542.*
Boas et al., Phosphatidylserine exposure and red cell viability in red cell aging and in hemolytic anemia, Proc. Natl. Acad. Sci, vol. 95, pp. 3077-3081, Mar. 1998.*
Rose et al., Control of Glycolysis in the Human Red Blod Cell, The Journal of Biological Chemistry, vol. 241, No. 21, Issue of Nov. 10, pp. 4848-4854, 1966.*
Int'l Search Report for PCT/IB2014/061338, five pages (dated Nov. 2014).
Written Opinion of ISA for PCT/IB2014/061338, six pages (dated Nov. 2014).
Int'l Preliminary Report on Patentability for PCT/IB2014/061338, 13 pages (dated Aug. 2015).
Buoni et al. "Betamethasone and improvement of neurological symptoms in ataxia-telangiectasia" *Archives of Neurology*, vol. 63, No. 10, p. 1479 (Oct. 2006).
Gill "Resealed erythrocytes as a potential drug carrier system" *International Journal of Pharmaceutical Sciences and Research*, vol. 3, No. 2, pp. 383-397 (Feb. 2012).
National Horizon Scanning Centre "Dexamethasone sodium phosphate (EryDex) for ataxia telangiectasia—first line" five pages (Feb. 2012).
Ropars et al. "Resealed red blood cells as a new blood transfusion product" *Bibliotheca Haematologica*, No. 51, pp. 82-91 (Jan. 1985).

* cited by examiner

*Primary Examiner* — Sharmila G Landau
*Assistant Examiner* — Stephen M Chong
(74) *Attorney, Agent, or Firm* — Sterne, Kessler, Goldstein & Fox P.L.L.C.

(57) ABSTRACT

The present invention relates to a process for preparing erythrocytes loaded with one or more substance of pharmaceutical interest. The present invention is also directed to loaded erythrocytes thus obtained and pharmaceutical compositions comprising said population of loaded erythrocytes as well as therapeutic application thereof, in particular in the treatment of Ataxia telangiectasia.

15 Claims, 4 Drawing Sheets

PROCESS FOR THE PREPARATION OF ERYTHROCYTES LOADED WITH ONE OR MORE SUBSTANCES OF PHARMACEUTICAL INTEREST AND SO OBTAINED ERYTHROCYTES

This application is the U.S. national phase of International Application No. PCT/IB2014/061338, filed 9 May 2014; which designated the U.S. and claims priority to Italian Application No. RM2013A000280, filed 10 May 2013, and Italian Application No. RM 2013A000610, filed 5 Nov. 2013; the entire contents of each of which are hereby incorporated by reference.

This invention relates to a process for preparing erythrocytes loaded with one or more active ingredients, the loaded erythrocytes thus obtained and pharmaceutical compositions comprising said the loaded erythrocytes.

The present invention is also directed to pharmaceutical compositions comprising said erythrocytes and therapeutic application thereof, in particular in the treatment of Ataxia telangiectasia.

STATE OF THE PRIOR ART

Red blood cells, also known as erythrocytes, are included in the state of the prior art among the drug carriers that are able to carry and release into circulation and/or direct active ingredients efficiently to target sites. The advantage of the use of erythrocytes as drug carriers lies mainly in the fact that the active ingredient can be kept in circulation for periods of days or weeks and anyhow for periods much longer than is normally the case when using oral or intravenous formulations or sustained release systems mediated by liposomes or other drug carriers. Moreover, once these carriers have performed their task carrying the active ingredient, they are removed from circulation via the physiological pathway for the elimination of native erythrocytes in the liver and spleen.

Numerous processes have been proposed to encapsulate active ingredients or contrast media in human or mammalian red blood cells for biomedical and clinical purposes.

In particular, patent EP0882448 described for the first time a process for encapsulating drugs in erythrocytes in concentrations sufficient to obtain the pharmacological effect desired. The process described in the prior patent mentioned above includes a series of operational steps that can be summarized as follows:

a first step in which the erythrocytes are swollen,
a second step in which the swollen erythrocytes are lysed to allow the opening of pores in the membrane of said erythrocytes large enough to allow the active ingredients of interest to cross inside the intracellular space,
a concentration step of the lysed erythrocytes
an encapsulation step in which the erythrocytes are brought into contact with the active ingredients, followed by a closing/resealing of the erythrocytes for the purpose of capturing the active ingredients in the red blood cells.

The process just described has made it possible to obtain erythrocytes loaded with active ingredients and suitable to be used as drug carriers. Currently, the most effective method of reference for encapsulating drugs in red blood cells is, for experts of the sector, the one described above.

However, in using this process it has been observed that in the concentration step of the lysed erythrocytes in the operating conditions defined in the patent specified above (EP0882448), these lysed erythrocytes are subject to a mechanical stress that may make the following step of reconstitution of the loaded erythrocytes rather difficult.

Among the various known techniques for encapsulating active ingredients in erythrocytes, the one described in patent EP1773452-B1 provides for a correction of the process parameters, such as the change of the flow rate of the lysis solution and the adjustment of the osmolality thereof, in order to obtain reproducibility in the encapsulation of the active ingredient as the patient's osmotic fragility (or globular osmotic resistance) varies.

The scope of the present invention is to further improve the already satisfactory results achieved with the process described in EP 0882448 in order to obtain an improved process for encapsulating substances of pharmaceutical interest in erythrocytes.

SUMMARY OF THE INVENTION

The present application relates to a process for preparing erythrocytes loaded with one or more substances of pharmaceutical interest which, compared to the same process described in the known state of the art, appears to be improved in several aspects.

In particular, this process comprises a series of operational steps, which are characterized by the fact that the concentration step of the erythrocytes is carried out before the cell lysis step, the latter necessary to allow the pharmaceutically active molecules to be encapsulated in the red blood cells. More precisely, this lysis step is carried out during the contact step with a solution comprising the substance to be encapsulated.

The process of the invention provides that the starting erythrocytes undergo two subsequent cell swelling steps, without lysis, using appropriate hypotonic solutions; in actual fact, these steps replace the swelling step and lysis step according to the same process of the prior art.

Therefore, the subject of the present invention is a process for preparing erythrocytes loaded with one or more substances of pharmaceutical interest, such as active ingredients, comprising steps in which:
a) the erythrocytes are swollen with a first hypotonic solution,
b) the erythrocytes obtained in step a) are further swollen, without reaching lysis, using a second hypotonic solution, which is more hypotonic than said first solution,
c) the erythrocytes obtained in step b) are concentrated,
d) the erythrocytes thus concentrated are put into contact with a lysis solution comprising one or more substances of pharmaceutical interest and subsequently
e) a sealing solution is added for obtaining a population of red blood cells loaded with said substances of pharmaceutical interest.

Advantageously the process may comprise an intermediate step (a2) between steps (a) and (b), wherein the first hypotonic solution is removed at least in part before adding the second hypotonic solution.

Further objects of the invention are the population of the erythrocytes loaded with one or more active ingredients obtainable by means of the above process and the pharmaceutical compositions comprising a population of erythrocytes loaded as defined above.

Further objects of the invention are pharmaceutical compositions comprising the erythrocytes loaded with one or more active ingredients obtained by the process above and said erythrocytes and compositions for use in the treatment of diseases e.g. Ataxia telangiectasia.

The invention is based on the surprising discovery that it is possible to encapsulate active ingredients in the erythrocytes subjected only to swelling and concentration steps without prior induction of hemolysis. Indeed, the opening of the pores (hemolysis) can be effectively obtained, after concentration, with the same solution containing the substances of interest. The new process is much more effective than the previous ones, and generates a final product (erythrocytes containing at least one pharmaceutically active substance) very similar to native erythrocytes (not subjected to the process).

Advantages Provided by the Invention

The operating changes introduced in the new process allow both to better preserve the plasma membrane of the red blood cells and to achieve a greater concentration, thereby providing a much higher encapsulation efficiency.

In the process of this invention, encapsulation of the substances of interest takes place with a better yield compared with the process described in the known state of the art, allowing the encapsulation of greater amount of therapeutically active substances. In particular, the inventors of this process have demonstrated that in order to achieve the same levels of active ingredient encapsulated, it is possible to use, in the process of the invention, a quantity of starting active ingredient significantly lower than that currently used with the standard process described in EP0882448. In particular, as also described in the experimental section, in order to encapsulate up to about 11 mg, for example, of dexamethasone sodium phosphate, with the same amount of red blood cells subjected to the treatment, about 500 mg of starting drug are needed with the process of the prior art and only 62.5 mg with the process described herein.

Moreover, this process has proven to be reproducible and reliable in encapsulating quantities of the substance of interest in red blood cells in proportion to the initial amount of said substance: these characteristics allow the clinical use of different doses, making it possible to administer doses commensurate to different clinical needs, varying only the amount of active ingredient added during the process.

The increased encapsulation efficiency was demonstrated not only with active molecules having low molecular weights (e.g., dexamethasone sodium phosphate as shown in Example 1), but also with molecules having high molecular weights. As reported in Example 5, proteins having molecular weights in the order of 110 kDa (dimers of yeast hexokinase—Hk—of 55 kDa) or in the order of 60 kDa (thymidine phosphorylase) have been effectively encapsulated.

Thanks to the modified sequence of the operational steps, significant improvements have been obtained also in the physiological parameters related to the population of loaded erythrocytes obtained by the process of the invention. In particular, as shown in the examples, the erythrocytes loaded using the process described herein have parameters, such as the mean cell volume and cell viability (metabolism), entirely comparable to those of untreated erythrocytes. Overall, the experimental data show that the new process is able to better preserve the cell size and cell content of the starting erythrocytes compared to the prior art, enabling, thus, to obtain a population of loaded erythrocytes significantly more similar to a population of untreated erythrocytes from a physiological perspective.

Comparative experiments carried out on the population of erythrocytes loaded according to the invention or with the analogous process of the prior art (EP0882448) have shown, for example, that the mean cell volume (MCV) of the red blood cells is about 86 femtoliters (present invention) and about 71 femtoliters (prior art) respectively, where the value of MCV for untreated erythrocytes is between 80 and 97 femtoliters. In addition, the amount of mean corpuscular hemoglobin (MCH) measured in the red blood cells subjected to the process herein and the one described in the state of the prior art were found to be about 21.2 picograms (much closer to normal) and about 14 picograms (prior art) respectively, with a value for untreated erythrocytes, which normally varies between 27.6 and 33.3.

The better overlap between erythrocytes loaded with this process and untreated erythrocytes is also confirmed by the increased cell viability (metabolism) observed. In particular, as described more in detail further below, the viability of the erythrocytes treated according to the present invention is significantly better in terms of both increased metabolic capacity and reduced presence of senescence markers. As discussed in more detail below, data relating to the greater cell viability (greater metabolism and less senescence markers) allow us to state that the process described herein is, in fact, capable of producing a population of loaded erythrocytes having a longer half-life compared to the erythrocytes obtained with the process of the prior art. It follows that the population of erythrocytes as per the invention allows for the transport of the encapsulated substances and/or their release for a period of time longer than that allowed by the erythrocytes loaded according to the process described in the prior art.

Thanks to the technical solutions described, the present invention also allows to overcome the limits of the method described in EP1773452-B1 and to obtain a reproducible encapsulation of active substance without correction of the process parameters for each individual patient, since the process is independent from both the different osmotic fragility of the patient's red blood cells (as demonstrated in Example 7) and the initial hematocrit (as demonstrated in Example 8).

The advantageous proprieties described above for the erythrocytes of the invention, especially the highest amount of the medicament encapsulated within the erythrocytes and their longer half-life make said erythrocytes effective in the treatment of different diseases, e.g. Ataxia telangiectasia.

DESCRIPTION OF THE FIGURES

FIG. 1 is a schematic representation of the process described herein compared to the process of the prior art (EP0882448).

FIG. 2 is a graph relating to the globular osmotic resistance (RGO) for two individuals, evaluated by measuring the total free hemoglobin based on osmolality. The RGO is also expressed as the osmolality at which 50% hemolysis, i.e., 50% of free hemoglobin, is observed.

DETAILED DESCRIPTION OF THE INVENTION

Glossary

Figure 1:
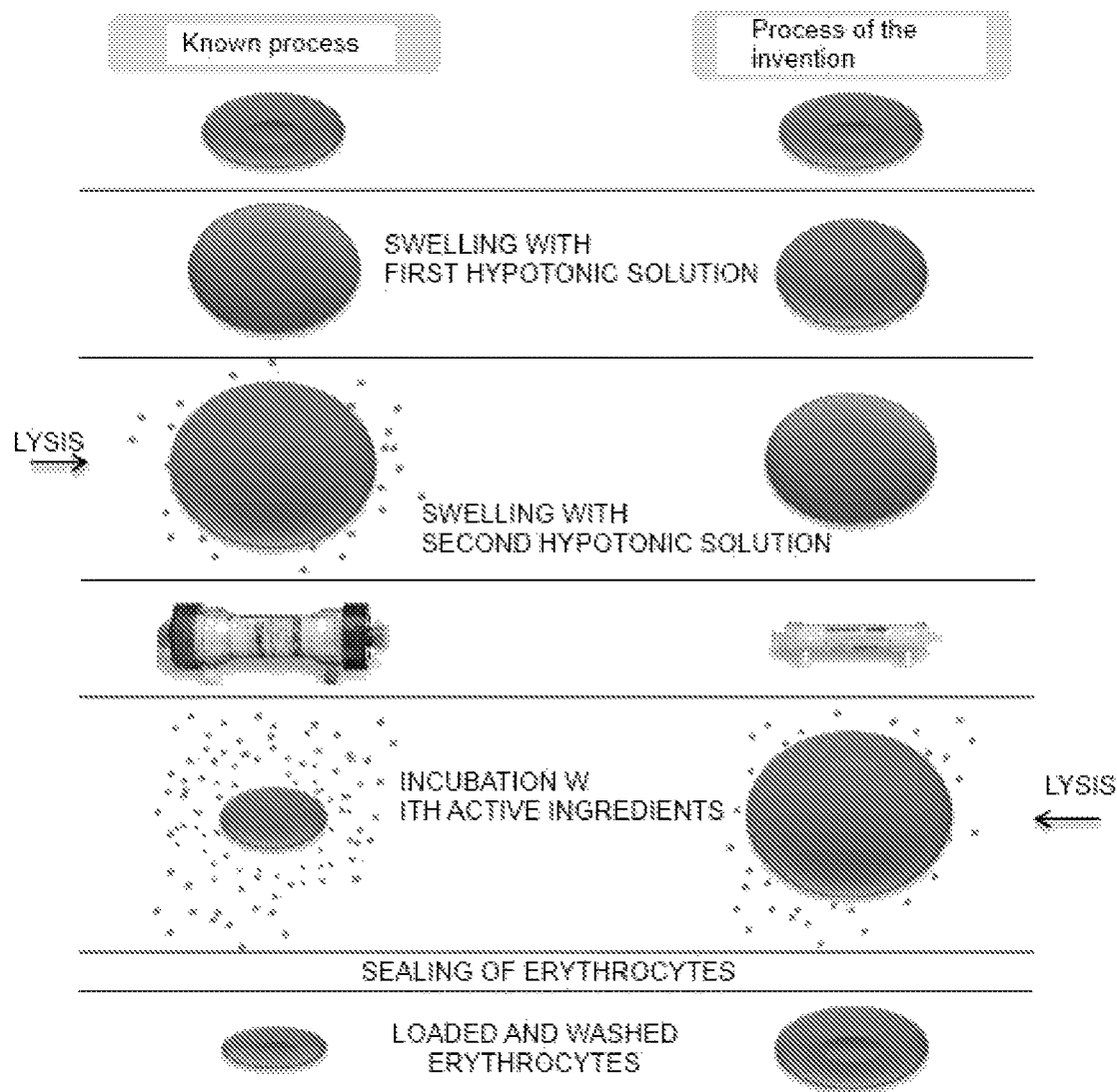
FIG. 1.
Figure 2:
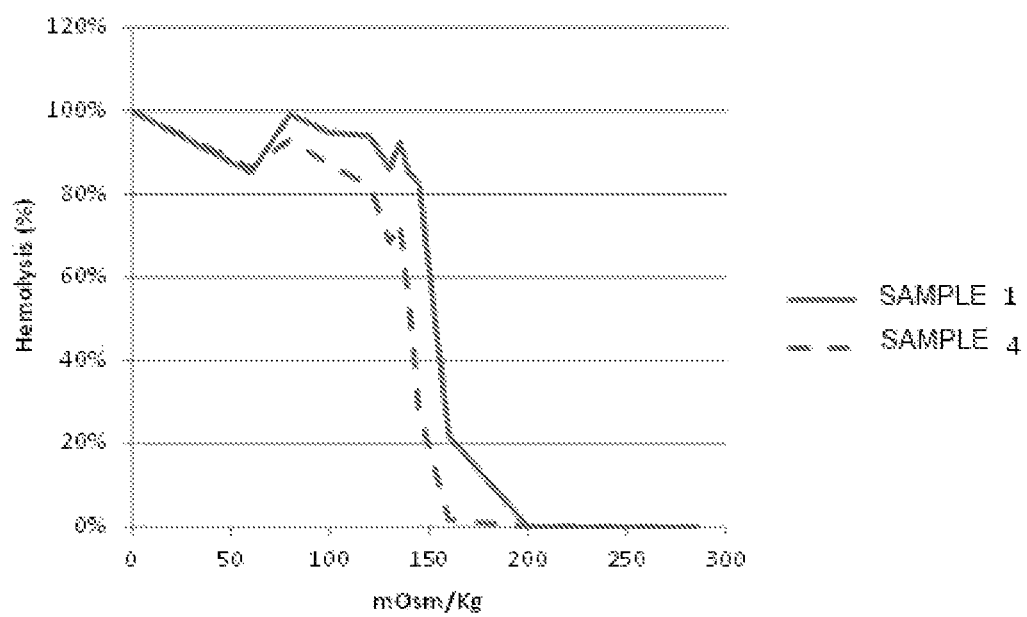
FIG. 2.

Some technical terms typical of the technical filed are explained below.

For the purposes of the present invention, the expression "swelling of the erythrocytes" means an increase in the volume and spherical form of the erythrocytes due to the increased internal pressure caused by the entry mainly of water, without, though, any phenomena of abnormal opening of the pores on the cell membrane or irreversible breakage thereof. Normally, swelling as understood in the present patent does not imply an outpour of cellular material.

For the purposes of the present invention, and in the specific technical field, the terms "lysis" or "hemolysis" or "partial lysis" mean the reversible opening of the pores on the cell membrane with consequent free passage in both directions of intra- and extra-cellular materials. Therefore, lysis is a phenomenon of temporary and reversible permeabilization and does not involve a complete and irreversible rupture of the cell membrane.

It follows that the term "lysed erythrocyte" refers to an erythrocyte whose plasma membrane features pores that can be reclosed in such a way that the integrity of the cell membrane is restored.

For the purposes of the present description, the expression "(re)sealing solution" means a solution used that is able to close the pores in the plasma membrane of the erythrocytes mainly through the outflow of water. This solution allows to encapsulate the substance(s) of pharmaceutical interest within the erythrocytes thanks to the opening of said pores.

In this description, the expression "loaded erythrocytes" means erythrocytes (also referred to as red blood cells) that encapsulate variable amounts of one or more substances of interest.

For the purposes of the present invention, the expression "sealed erythrocytes" refers to red blood cells which, unlike the lysed erythrocyte, feature a plasma membrane permeability comparable to (overlapping with) that of untreated red blood cells.

In order to implement the process of the invention, the starting erythrocytes may be obtained by collection and isolation of red blood cells from an individual's blood sample. The starting sample is preferably treated with an anti-coagulant, such as heparin, in order to prevent coagulation thereof.

Optionally, the erythrocytes, before being subjected to the treatment according to the invention, can be isolated and subjected to one or more washings with saline solution in order to obtain a population of starting erythrocytes in which there are no or only negligible concentrations of contaminants, such as plasma, platelets, lymphocytes, etc.

Step (a):

As indicated above, the process comprises a step a) in which the population of erythrocytes is swollen initially through the use of a first hypotonic solution.

In one embodiment of the invention, the first hypotonic solution has an osmolality of between 230 and 150 mOsm/kg and, for example, a preferred osmolality of 180 mOsm/kg. In any case, the osmolality and the volume of the first solution are such that contact with this first solution makes the red blood cells reach an osmolality in the range from 250 to 200 mOsm/kg. In particular, the first hypotonic solution can be obtained, for example, by mixing 5 volumes of saline solution and 3 volumes of sterile distilled water. By way of non-limiting example, step (a) can be carried out maintaining the erythrocytes in about 300 mL of the first solution at a concentration (hematocrit) of about 3 to 7%, for a time of about 5 minutes at room temperature.

Step a) may be optionally followed by a step to remove, at least in part, the first hypotonic solution from the swollen erythrocytes. Such removal can be obtained, for example, by gentle centrifugation of the treated erythrocytes and separation of the supernatant.

Step (b):

The swollen erythrocytes obtained as described above are then subjected to further swelling through the use of a second hypotonic solution (step b). The second solution is characterized by the fact that it is more hypotonic than the first solution. The tonicity of the second solution is chosen in such a way as to cause further swelling of the erythrocytes, without, however, causing the lysis thereof, which would cause the consequent outpour of intracellular material. The hypo tonicity conditions are controlled in such a way to avoid the induction of excessive cell fragility in view of the next concentration step of the erythrocytes. The osmolality values of the second hypotonic solution are determined experimentally in the laboratory and are constant in the process. The osmolality of the second solution is such as to induce a state of swelling in the red blood cells but without this leading to the opening of pores on their surface, thereby causing the initial outflow of cellular content and an excessive fragility of the erythrocytes.

The second hypotonic solution has an osmolality in the range from 80 to 170 mOsm/kg. In a preferred embodiment, the osmolality of the second solution is about 120 mOsm/kg. In any case, the osmolality and the volume of the second solution are such that contact with this second solution makes the red blood cells reach an osmolality in the range from 200 to 170 mOsm/kg.

In particular, the second hypotonic solution can be obtained, for example, by mixing 5 volumes of saline solution and 7 volumes of sterile distilled water.

By way of example, step (b) can be carried out maintaining the erythrocytes in about 64 mL of the second solution at a concentration (hematocrit) of about 8 to 15%, for a time of about 5 minutes at room temperature.

Step (c):

The swollen erythrocytes resulting from steps a) and b) above are then subjected to a concentration step c). Any known technology suitable for the concentration of a sample of erythrocytes, such as example, hemofiltration, centrifugation or dialysis, can be used to concentrate the swollen erythrocytes. In a preferred embodiment of the invention, the concentration is carried out by hemofiltration.

In particular, in the hemofiltration, any hemoconcentration filter (or even dialysate filter), known to experts in the art, can be used to separate the cellular portion from the liquid in which it is suspended in order to reduce the suspension volume, and hence concentrate the swollen erythrocytes. In general, the lower the volume of the hemoconcentration filter (for example, sizes for neonatal or pediatric use), the higher the level of hemoconcentration that can be reached.

Hemoconcentration is preferably carried out at room temperature for a time varying between 15 and 35 minutes. In general, the concentration of erythrocytes (hematocrit) obtained at the end of step c) is above 30%, for example 35%, 40%, 45%, 50%, 55%, 60%, 65%. In this concentration step, the osmolality of the suspension of erythrocytes is nearly constant, varying only a few units of mOsm/kg compared to the osmolality obtained after contact with the second hypotonic solution used in the previous step b).

Since the concentration step is carried out on red blood cells that are swollen but essentially intact in their structure, i.e., not lysed, the process described herein significantly reduces the risk of obtaining erythrocytes irreversibly damaged to the point that they can no longer be effectively used as a drug carrier. In fact, the optimal purpose of the process is that of obtaining a population of loaded and "reconstituted" erythrocytes with characteristics as close as possible to the physiological characteristics of the starting population and still able to perform the role of carrier in an efficient manner and for long periods of time.

Step (d):

The erythrocytes thus concentrated are then put into contact with a lysis hypotonic solution comprising one or more substances of pharmaceutical interest (step d). The characteristic of this solution is that it lowers the osmolality of the red blood cells to the point of causing their temporary lysis, that is, the reversible opening of the pores in the cell membrane. The solution containing the active ingredients may be, for example, an aqueous solution with low osmolality.

In a preferred embodiment of the invention, the lysis solution has an osmolality ranging from 10 to 100 mOsm/kg. In any case, the osmolality and the volume of the lysis solution are such that contact with the lysis solution makes the red blood cells reach an osmolality in the range from 150 to 110 mOsm/kg.

This solution, besides being hypotonic, contains the substance(s) of interest to be encapsulated. The permeabilization of the plasma membrane of the erythrocytes will thus favor their diffusion within the cell.

By way of example, step (d) can be carried out maintaining the erythrocytes, at a concentration (hematocrit) of 30-65%, in contact with the lysis solution containing the active substances, for a time of about 10 minutes at room temperature.

Step (e):

In order to encapsulate the molecule(s) of interest within the erythrocytes, a sealing solution is used to restore the parameters of the treated erythrocytes as close as possible to the physiological conditions. The sealing solution is a hypertonic solution with an osmolality in the range from 300 to 5000 mOsm/kg.

In a specific embodiment of the invention, the sealing solution used is a solution of Phosphate-Inosine-Glucose-Pyruvate-Adenine (PIGPA). Therefore, it is possible to obtain a similar closure effect with any hypertonic solution composed, for example, of distilled water and minerals or other nutrients used by red blood cells. However, the PIGPA hypertonic solution is to be preferred since it comprises nutrients that help the cell restore part of the lost content as well as cellular metabolic functions. In this regard, the resealing of the pores is favored and the normal membrane structure is restored (re-annealing).

By way of example, the sealing solution preferably has the following composition: 33 mM $NaH_2PO_4$, 1.606 M KCl, 0.194 M NaCl, 0.1 M inosine, 5 mM adenine, 20 mM ATP, 0.1 M glucose, 0.1 M pyruvate, and 4 mM $MgCl_2$. By way of example, about 3 mL of the sealing solution can be used for a volume of about 35 to 55 mL of lysed erythrocytes at a concentration (hematocrit) of about 15-40%. In particular, the contact of the sealing solution with the erythrocytes can be carried out for example for about 30 minutes, preferably at a temperature of 37° C. In this stage, the red blood cell suspension is brought to an osmolality at least equal to or greater than physiological levels. Although the temperature of 37° C. is not essential, it contributes to the rapid and optimal recovery of metabolic processes within the cell.

The substances of pharmaceutical interest to be encapsulated, either alone or in combination, in the red blood cells may be selected from those known according to the specific treatment needs required.

In one embodiment of the invention, the compounds of pharmaceutical interest are chosen from the following groups: active ingredients chosen from peptides, oligopeptides, polypeptides, proteins; active ingredients selected from oligonucleotides, nucleotide analogs, nucleosides, nucleoside analogs; active ingredients selected from hormones, immunosuppressant, inhibitors of malignant cell growth, corticosteroids, glucocorticoids, anti-retroviral and non-steroidal anti-inflammatory agents, cytokines, toxins, substances with vaccinating action; contrast media for diagnostics; particles or nanoparticles selected from nanoparticles containing a metal, magnetic nanoparticles, superparamagnetic nanoparticles (SPIO), and nanoparticle-active molecule complexes.

For example, substances can be chosen from 6-mercaptopurine, fludarabine phosphate, phosphorylated azidothymidine, dideoxycytosine, dideoxyinosine, glutathione, bisphosphonates, prednisolone, prednisolone sodium phosphate, dexamethasone, dexamethasone sodium phosphate, betamethasone, betamethasone sodium phosphate, thymidine phosphorylase, phenylalanine ammonia lyase, indocyanine green, and super-paramagnetic particles. Preferred active substances are dexamethasone and beta dexamethasone, also in form of phosphate, and deflazacort, whereas the active substance most preferred is dexamethasone sodium phosphate. In one embodiment of the present invention, the active ingredients may also include pro-drugs, namely precursors of bioactive ingredients. By way of non-limiting example, this pro-drug can be dexamethasone sodium phosphate (or dexamethasone 21-phosphate), which, once encapsulated in the red blood cell and administered to the patient, is converted, through a mechanism of endogenous activation (dephosphorylation) into the active anti-inflammatory drug called dexamethasone. Alternatively, the conversion from pro-drug to drug can be obtained by co-administration of the adequate activator in the same erythrocyte, in case there is no mechanism of endogenous activation.

A further object of the present invention is a population of erythrocytes loaded with one or more substances of pharmaceutical interest obtainable by the process described above.

As already indicated, the population of erythrocytes obtained with the process of the present invention shows greater cell viability (metabolism and survival) compared to the same population obtained with the method described in the literature. In particular, the erythrocytes treated according to the present invention have a cell half-life, evaluated in terms of percentage of phosphatidylserine measured with the annexin V assay, very similar to that of native erythrocytes. The annexin V assay is carried out in laboratory practice by the lab technician and has already been described in the literature (Canonico B. et al. 2010). Therefore, no further details are provided here. Said assay measures the percentage of erythrocytes that express phosphatidylserine on the outer surface of the plasma membrane whose presence is indicative of damage and accelerated cell aging via the natural elimination mechanism. In general, the red blood cells with exposed phosphatidylserine are subject to phagocytosis and are eliminated from the bloodstream more rapidly than erythrocytes that do not have this protein on the outer membrane. It follows that the lower the percentage of erythrocytes with phosphatidylserine exposure is, the greater the half-life of erythrocytes put into circulation in the human body will predictably be. The increased half-life is reflected in the longer release time of the medication or the longer transport time in the bloodstream. In the population of erythrocytes loaded with the process of the invention, average percentages of phosphatidylserine exposure below 10% are observed, for example, 9%, 8%, 7%, 6%, 5%, 4%, 3%, 2%, while the corresponding value of phosphatidylserine exposure on erythrocytes treated with other processes may exceed 20-40%. These results demonstrate that the process of the invention allows to obtain carrier erythrocytes, which, having an almost natural predictable half-life, carry in the bloodstream and/or release the encapsulated substances for a period of time sufficiently long enough to meet the most common pharmacological needs.

The excellent viability of the population of erythrocytes described herein is also confirmed by the evaluation of the metabolic capacity of the erythrocytes obtained. The evaluation of the metabolic capacity, as is known to experts of the sector, is indicative of the ability of a cell to preserve the biochemical functions necessary for its survival. Red blood cells are cells whose energy production is essentially based on the biochemical pathway of glycolysis in which lactate is the final product. It has been demonstrated for the population of erythrocytes forming the object of this application that the average amount of lactate produced for every $10^6$ erythrocytes is greater than 0.100 nmol/h, i.e., very similar to that of native erythrocytes.

The biochemical/molecular characteristics described above, relative to the population of erythrocytes forming the object of the present application, indicate that this population can be used more efficiently as a carrier for active ingredients than the population of erythrocytes described in the state of the prior art, since it is characterized by greater viability and a predictably longer half-life.

A further object of the present invention is a pharmaceutical composition comprising loaded erythrocytes obtained according to the invention and a pharmacologically acceptable excipient.

The compositions described herein are compositions suitable for administration of erythrocytes and appropriate to reach the target site of pharmacological interest. Therefore, these are compositions for parenteral administration preferably in a physiological solution, but also, for example, aqueous suspensions (including glucose) or those formulated as described in the prior art. By way of non-limiting example, water or buffers, integrated with preservatives, stabilizers, sugars and minerals etc. can be used as pharmacologically acceptable excipients. Such compositions may also be in lyophilized form for storage and reconstituted in a suitable carrier prior to use.

The process of the present application may be performed with any known apparatus suitable for hemofiltration with handling of different solutions and control of flows, osmolality and volumes. Preferably, the apparatus and the process are operated automatically based on a suitable program, for example by using a medical electrical apparatus called Red Cell Loader.

Figure 3:
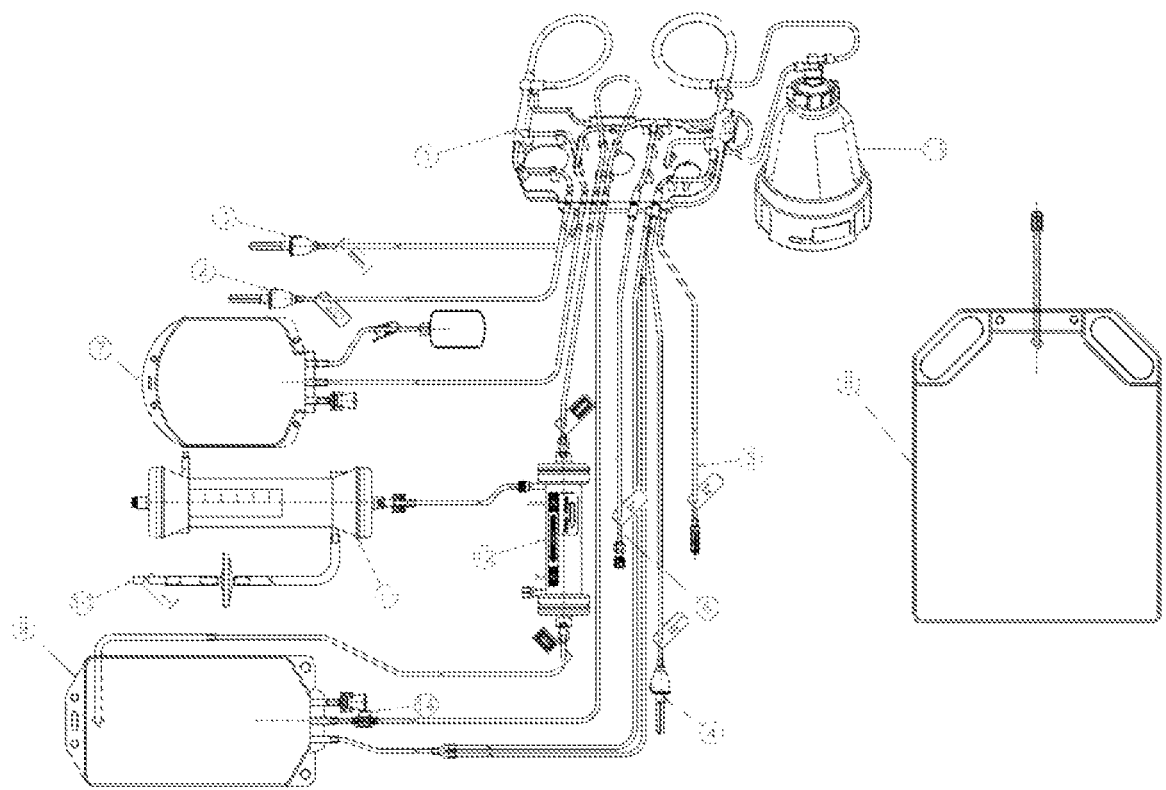
FIG. 3: Representation of a kit suitable for the execution of the process of the invention when used in conjunction with a medical device as described in BO2010A000255.

An example of a kit to carry out the process as per the claim, to be used in conjunction with equipment described in the previous Italian patent application BO2010A000255, is shown in FIG. 3. The kit contains the following numbered structural elements:

(1) Spike connector for hypotonic solution 1
(2) Spike connector for hypotonic solution 2
(3) Spike connector for 2-liter bag of injectable saline solution (washing)
(4) Connector for waste bag
(5) Luer connector for the input of 50 mL of patient's blood (50 mL syringe)
(6) Final collection bag
(7) Waste bag
(8) Transfer bag
(9) Connector for pump to the Red Cell Loader (right side of machine, stand pole side)
(10) Reservoir (for ultrafiltrate)
(11) Hemoconcentration filter
(12) Bowl (Latham bowl for blood separation and washing)
(13) Pierceable point (for input of drug and PIGPA sealing solution).

Any type of disease that needs a treatment by suitable encapsulable medicament of the active ingredient may be advantageously treated with the erythrocytes of the invention. An example of said diseases is Ataxia telangiectasia (AT) treated with dexamethasone, preferably dexamethasone sodium phosphate.

L'AT is a rare genetic, autosomal recessive, pathology caused by the mutation of ATM gene with an incidence of 1:40,000/1:300.000. The AT causes a progressive neurodegeneration of the cerebellum that causes progressive ataxia (motor disorganization). It can be defined at around 2 years of life and its degeneration is quite fast, normally leading to confinement in a wheelchair around the second decade of life. The major neurological symptoms are cerebellar dysarthria, dysmetria and no coordination of eye movements to which extrapyramidal symptoms such as chorea or bradykinesia can accumulate. The patients are very susceptible to infection and normally die after 20 years due to severe pulmonary complications or onset of leukemia.

EXAMPLES

The invention is described below with all the experimental details in the following examples, which are purely descriptive and not limiting for the present invention.

Example 1

Process for Loading Erythrocytes

The process for loading erythrocytes was carried out using the apparatus described in patent application (IT) BO2010A 000255 & U.S. 61/373,018 as detailed below.

The erythrocytes, separated from 50 mL of whole blood by means of a centrifugal system of the "Latham Bowl" type spinning at 5600 rpm, are washed with 750 mL of saline solution at a washing speed of 225 mL/min and transferred into the transfer bag.

A quantity of 300 mL of a first hypotonic solution having an osmolality of 200 mOsm/kg is added to the transfer bag, which is then incubated on a stir plate at room temperature for 5 minutes. The first hypotonic solution is then removed by centrifugation (Bowl) until a volume of about 80 mL is reached.

The erythrocytes thus concentrated are transferred back into the transfer bag to which 64 mL of a second hypotonic solution with an osmolality of 180 mOsm/kg are then added.

The bag is then incubated at room temperature on a plate under stirring for 5 minutes. After incubation, the erythrocytes are concentrated using a hemoconcentration filter and about 80 mL of ultrafiltrate is collected in the reservoir to which a slight negative pressure is applied by means of a vacuum pump. The erythrocytes thus concentrated are then retrieved and transferred to a transfer bag. The drug of interest, in this example dexamethasone sodium phosphate (25 mg/mL), was pre-mixed with approximately 11 mL of water for injectable solutions (the preparation has an osmolality of about 20 mOsm/kg) and added to the concentrated erythrocytes by injection in the transfer bag. This operation must be carried out in 5 minutes. The content of the transfer bag is then incubated at room temperature on a plate under stirring for 10 minutes. A quantity of 3 mL of a sealing solution (with an osmolality of 3800 mOsm/kg) is then added. This addition must be made in 5 minutes. The transfer bag is incubated for 30 minutes at 37° C.±2 on the stir plate. The erythrocytes are then transferred into the bowl and washed thoroughly with 1100 mL of saline solution at a flow rate of 225 mL/min. Finally, the loaded erythrocytes thus obtained are transferred to a final collection bag. The total time of the process is approximately 1 h and 30 min.

Example 2

Encapsulation Efficacy

The process described in the present invention provides an encapsulation efficiency (introduction) of the active ingredient (in this example, dexamethasone sodium phosphate) almost 10 times greater than the known method (process 1), as shown in Table 1.

In particular, 50 mL of whole blood were used as starting material. During the active ingredient loading phase (step d) of the process described above, 20 mL of DSP (dexamethasone sodium phosphate) 25 mg/mL are added for the known method (i.e. according to EP0882448) and only 2.5 mL of the same solution of DSP added with 11 mL of water for injection in the process of the present invention (process 2).

The analysis of the DSP content in the erythrocytes loaded as per process 1 or 2 was performed using HPLC equipment after extraction of the active ingredient from the inside of the red blood cells by boiling and dilution in water and methanol. The results are reported in Table 1.

TABLE 1

|  |  | Known Process 500 mg of DSP starting dose | Process object of the present specification 62.5 mg of DSP starting dose |
|---|---|---|---|
| encapsulated DSP at the end of the process (mean) | mg/bag | 8.9 | 11.2 |

Example 3

Lactate Production in Erythrocytes

A bag of whole blood from a healthy donor was used. An initial portion of the donor's red blood cells was used as the untreated sample. An amount of 50 mL of whole blood was processed using the process of the present invention. At the end of the process, 30 mL of treated erythrocytes were collected and brought to 40% hematocrit by centrifugation. Glucose is then added to each sample and these are incubated at 37° C. for 3 hours, analyzing the accumulation of lactate in the supernatant (transformation of glucose into lactate via glycolytic pathway) every 30 minutes. The analysis was performed through the use of a blood gas analyzer.

The lactate production of the untreated RBCs (red blood cells) is comparable to the lactate production of RBCs obtained with the process described herein. This result indicates that the red blood cells obtained by the process forming the object of the present invention are able to maintain their main metabolic function (glycolysis) transforming glucose into lactate with an efficiency similar to that of the untreated red blood cells (control), as shown in table 2.

TABLE 2

|  |  | Untreated RBCS | Process described herein 250 mg of DSP Initial quantity |
|---|---|---|---|
| Lactate production | mol $10^6$ RBC/h | 0.138 | 0.130 |

Example 4

Half-Life of Loaded Erythrocytes

The estimated half-life of the erythrocytes loaded according to the process described herein was evaluated by measuring the annexin V on the cell surface, known to be a marker of cell death (senescence), as detailed below.

In particular, a bag of whole blood from a healthy donor was used. An initial portion of the donor's red blood cells was used as the untreated sample. An amount of 50 mL of whole blood was processed using the process of the present invention. An amount of $10^6$ erythrocytes was drawn from the final product of the process and from the untreated sample; they were diluted in a reaction buffer for annexin V, 3 μl of annexin V conjugated with FITC fluorochrome were added and the analysis by flow cytometry was carried out.

As shown in Table 3 below, the increase in annexin V from 0.75% in the untreated control to 6.26% of the red blood cells obtained with the process described herein is indicative of the fact that the latter still have a high capacity of remaining in circulation for a long time. For products based on red blood cells for transfusion purposes, the literature reports annexin V values similar to those obtained for the loaded red blood cells obtained with the process described herein (Relevy H. et al., 2008).

TABLE 3

|  |  | Untreated RBCs | Process described herein 250 mg of DSP initial quantity |
|---|---|---|---|
| Annexin V | % | 0.75 | 6.26 |

Example 5

Variation of Encapsulated Dose

The process of the present invention allows for the encapsulation of doses of active ingredient, such as DSP (dexamethasone sodium phosphate), in a very broad therapeutic range by simply varying the initial dose of drug used, as shown in Table 4 below. In particular, 50 mL of whole blood was used for each experiment and for each initial amount of DSP. An amount of 20 mL of DSP 25 mg/mL was added for the loading of the DSP according to the known method (EP0882448).

In the case of the process described herein, 10 mL, 5 mL, 2.5 mL and 2 mL of DPS 25 mg/mL, premixed each in 11 mL of water for injection, were added for the doses of 250, 125, 62.5 and 50, respectively. The analysis of the DSP encapsulated in red blood cells requires first a 1:10 dilution in distilled water, a sample boiling step to denature the proteins, followed by centrifugation and extraction in water and methanol. The analysis of the encapsulated DSP was performed by HPLC. The results are reported in Table 4.

TABLE 4

|  |  | Known process | Process described herein |  |  |  |
|---|---|---|---|---|---|---|
| Initial quantity DSP | mg | 500 | 250 | 125 | 62.5 | 50 |
| DSP encapsulated dose | mg | 8.9 | 29.4 | 18.3 | 11.2 | 9.9 |

Example 6

Encapsulation of Active Ingredients of High Molecular Weight

The process of the present description also allows for the encapsulation of proteins of high molecular weight such as Hexokinase (HK) with an encapsulation efficiency of the initial product greater than 15%, as shown in Table 5 below.

In particular, 50 mL of whole blood from healthy donors that were subjected to the encapsulation process described herein were used. The active ingredient encapsulated was the protein Hexokinase. In the active ingredient addition step, 200 mg of HK dissolved in 14 mL of water for injection were added.

TABLE 5

|  |  | Process described herein |
|---|---|---|
| Initial amount of protein HK | IU/total | 10000 |
| Hexokinase (HK) encapsulated at end of | IU/total | 1600 |

Example 7

Influence of Globular Osmotic Resistance on Loading of Erythrocytes

Every individual has his own globular osmotic resistance (RGO) that can affect the outcome of the loading process. The data presented below indicate that donors with different osmotic strengths maintain very similar drug loadings. Therefore, the process of the present invention has proven not to be significantly affected by the patient's initial RGO as illustrated by the data in Table 6, differently from what is indicated for similar known methods.

To determine the variability of product loading inside the red blood cells based on the RGO of different individuals, the process described in the present invention was used with an initial dose of DSP (dexamethasone sodium phosphate) equal to 50 mg. A total of 5 tests was performed starting from 50 mL of whole blood from 5 different individuals with different RGOs.

The osmotic globular resistance of each individual was measured by diluting a portion of their whole blood in solutions with decreasing concentration of NaCl (8 different values of osmolality), by measuring the free hemoglobin in each of the solutions and building the graph of total free hemoglobin as a function of the osmolality (see FIG. 1). The value of RGO (corresponding to the osmolality at 50% of hemolysis or 50% of free hemoglobin) was then obtained by interpolation of said curves obtained. The released hemoglobin was quantified by means of Drabkin's reagent with spectrophotometer reading (Drabkin DL. Med Sci 1949). The analysis of the DSP (dexamethasone sodium phosphate) loaded in the final erythrocytes was performed after lysis thereof by boiling, extraction in water-methanol and HPLC. The results are reported in Table 6.

TABLE 6

| Sample | RGO (Hemolysis mOsm/kg) | RGO (Hemolysis 50%) NaCl concentration | DSP loading mg/bag |
|---|---|---|---|
| 1 | 153 | 0.47 | 9.6 |
| 2 | 143 | 0.44 | 10.5 |
| 3 | 151 | 0.47 | 9.8 |
| 4 | 141 | 0.43 | 10.2 |
| 5 | 143 | 0.44 | 9.9 |
| medium | 146 ± 5 | 0.45 ± 0.02 | 10.0 ± 0.4 |

As shown in Table 6 above, in the process described herein the loading of dexamethasone sodium phosphate (DSP) in red blood cells of individuals with different initial RGOs (from 141 to 153 mOsm/kg) did not show changes such that it can assumed that there is a pharmacologically different effect (average load of 10.0±0.4 mg/bag). The variation of encapsulated DSP compared with the variation of an individual's RGO as described in these examples is negligible from the pharmacological point of view.

Example 8

Influence of the Variation of Initial Hematocrit on Loading of Erythrocytes

To determine the variability of loading of the red blood cells based on the hematocrit of the initial blood, the process described in the present invention was used with an initial dose of DSP (dexamethasone sodium phosphate) equal to 62.5 mg.

A total of 10 tests were performed with 5 different individuals (1 hematocrit test with about 40% hematocrit and 1 test with about 50% hematocrit for each donor). The standardization of the hematocrit for each donor was carried out by centrifugation or dilution of the initial blood. The analysis of the DSP loaded in the final erythrocytes was performed after lysis thereof by boiling, extraction in water-methanol and HPLC. The results are reported in Table 7.

TABLE 7

|  | Initial blood HCT adjusted at 40% | | Initial blood HCT adjusted at 50% | |
|---|---|---|---|---|
| Sample | HCT (%) | DSP loaded (mg/final bag) | (%) | DSP loaded (mg/final bag) |
| 1 | 39.9 | 11.48 | 49.9 | 13.04 |
| 2 | 40.0 | 11.72 | 50.1 | 10.76 |
| 3 | 39.3 | 10.94 | 50.0 | 10.52 |
| 4 | 40.8 | 11.75 | 50.0 | 11.70 |
| 5 | 40.0 | 11.16 | 50.1 | 9.92 |
| average | 40.0 ± 0.5 | 11.41 ± 0.65 | 50.0 ± 0.1 | 11.19 ± 1.22 |

As shown by the data reported in Table 7, the loading of dexamethasone sodium phosphate in red blood cells of individuals with different initial hematocrit values (hematocrit from 40% to 50%) is extremely constant (from 11.41 to 11.19 mg/final bag) and shows no variations of statistical significance (p>0.05 with t-Student test for paired data) with no need to vary process parameters described herein. The variation of encapsulated DSP compared with a 10% variation of the initial hematocrit, which on the contrary is a highly significant variation (p<0.001 in t-Student test for paired data) of the individuals described in these examples, is negligible from the pharmacological point of view.

Example 9

Treatment of AT with the Erythrocytes of the Prior Art and the Invention

Clinical Study IEDAT-01

A Clinical study called IEDAT-01 (or IEDAT), was carried out at two Italian university centers Brescia—Rome—Civil Hospital and La Sapienza University. Patients with Ataxia—Telangiectasia enrolled in the study were treated with dexamethasone sodium phosphate encapsulated in erythrocytes produced according to the previous technology according to EP0882448 (Old Procedure). This was a prospective, open study of a period of 6 months. The patients received the therapy EryDex, ie dexamethasone sodium phosphate encapsulated in erythrocytes from the patients themselves, at monthly intervals.

A total of 22 patients were enrolled between the ages of 4 and 19 years, 18 of which have regularly completed the treatment provided for 6 months. The primary efficacy endpoint of the study was measured by the rating scale ICARS ("International Cooperative Ataxia Rating Scale"), which assesses changes in neurological symptoms, comparing the values obtained at the end of the 6 month treatment period with respect to the values obtained ICARS before starting the treatment (baseline). The results for the primary endpoint (p=0.02) and those of the secondary endpoints of the study were statistically significant. This is both in the analysis Intent to Treat (ITT) population, which includes all 22 patients who entered the study even if they have not ended it, and in analysis Per protocol (PP), which instead considers only the patients who completed the 6 months treatment.

From the point of view of safety, the treatment is found to be well tolerated by the patients included in the study.

ICARS

The scale ICARS ("International Ataxia Rating Scale"), developed by Trouillas in 1997, is the most frequently tool used by neurologists to assess and standardize the most common neurological manifestations of syndromes related to cerebellar dysfunction (cerebellum), as the Ataxia. The ICARS was used as an outcome measure in various interventional clinical trials, especially in Friedrich's ataxia. It is a semi-quantitative scale divided into 4 sub scales related to the following domains: abnormal posture and abnormal gait; kinetic functions; oculomotor disorders and language disorders. The maximum total score is 100 points (0 corresponds to the healthy subjects, 100 to the worst degree of patient status).

IEDAT, Compassionate Study and Neurological Improvements with Old and New Procedure The IEDAT study was carried out on 22 patients AT and its aim was to measure the effect of EryDex treatment (Dexamethasone sodium phosphate encapsulated in autologous red blood cells according to the procedure known) on the neurological status of patients through the scale ICARS.

4 patients who participated in the IEDAT study continued the treatment with EryDex after the end of the study in a clinical protocol so-called "Compassionate Use".

During IEDAT the study were used erythrocytes loaded with dexamethasone phosphate by the procedure (EryDex OLD procedures, as described in patent EP0882448). The 4 patients who entered in compassionate use continued the treatment EryDex using the OLD procedures then moved (after an average of 5 treatments) to the treatment with EryDex obtained by the procedure described according to this application (EryDex, NEW Procedures). This procedure leads to significant improvements compared to the previous procedure.

Table 8 below shows that the treatment of 4 patients AT with the OLD procedures has resulted in an improvement of 3.25 points in the scale ICARS after 5 months of continued treatment with compassionate use compared to the baseline of the ICARS study. This value corresponding to an improvement percentage of 5.9% is to be considered modest from a clinical point of view. An improvement of the ICARS scale less than 10% is in fact generally regarded as insignificant by Neurologists.

The benefits observed in 4 patients after switching to the EryDex treatment obtained with the new procedure are particularly evident. The average improvement was in fact 6.75 points ICARS (13.1%) compared to the value of ICARS observed after treatment with the OLD procedures. The NEW Procedures, thanks to the improvements of certain characteristics of red blood cells (most similar to red blood cells of the patient) and better reproducibility of encapsulation of the drug, has allowed to obtain an improvement in neurological high relevant from a clinical point of view. A total of 4 patients treated with EryDex, from the beginning of the IEDAT study until the end of the Compassionate Study, had an average improvement of the ICARS values of 10 points, or 18.3% (last column of the table below). This data is of even more importance when compared to what has been observed in patients AT that during the examination period have not received the EryDex treatment and that on average had a worsening of 7 points in the ICARS scale.

TABLE 8

| | OLD Procedure | | | | NEW Procedure | | |
|---|---|---|---|---|---|---|---|
| | ICARS Values - IEDAT STUDY | | | ICARS Values - COMPASSIONATE USE | | | |
| PATIENT | Baseline | Last Visit | Delta Baseline - Last Visit | End Treatments OLD Procedure | Delta Baseline - OLD Procedure | End Treatments New Procedure | Delta End OLD Procedure - End New Procedure | Delta Baseline - End New Procedure |
| 02-01 | 57 | 53 | −4 | 47 | −10 | 45 | −2 | −12 |
| 02-02 | 55 | 58 | 3 | 58 | 3 | 53 | −5 | −2 |
| 02-05 | 58 | 56 | −2 | 54 | −4 | 41 | −13 | −17 |

TABLE 8-continued

| | OLD Procedure | | | | | NEW Procedure | | |
| | ICARS Values - IEDAT STUDY | | | ICARS Values - COMPASSIONATE USE | | | | |
| PATIENT | Baseline | Last Visit | Delta Baseline - Last Visit | End Treatments OLD Procedure | Delta Baseline - OLD Procedure | End Treatments New Procedure | Delta End OLD Procedure - End New Procedure | Delta Baseline - End New Procedure |
|---|---|---|---|---|---|---|---|---|
| 02-08 | 49 | 42 | -7 | 47 | -2 | 40 | -7 | -9 |
| MEAN | 54.75 | 52.25 | -2.5 | 51.5 | -3.25 | 44.75 | -6.75 | -10 |
| ICARS improvement % | | | 4.6 | | 5.9 | | 13.1 | 18.3 |

Figure 4:
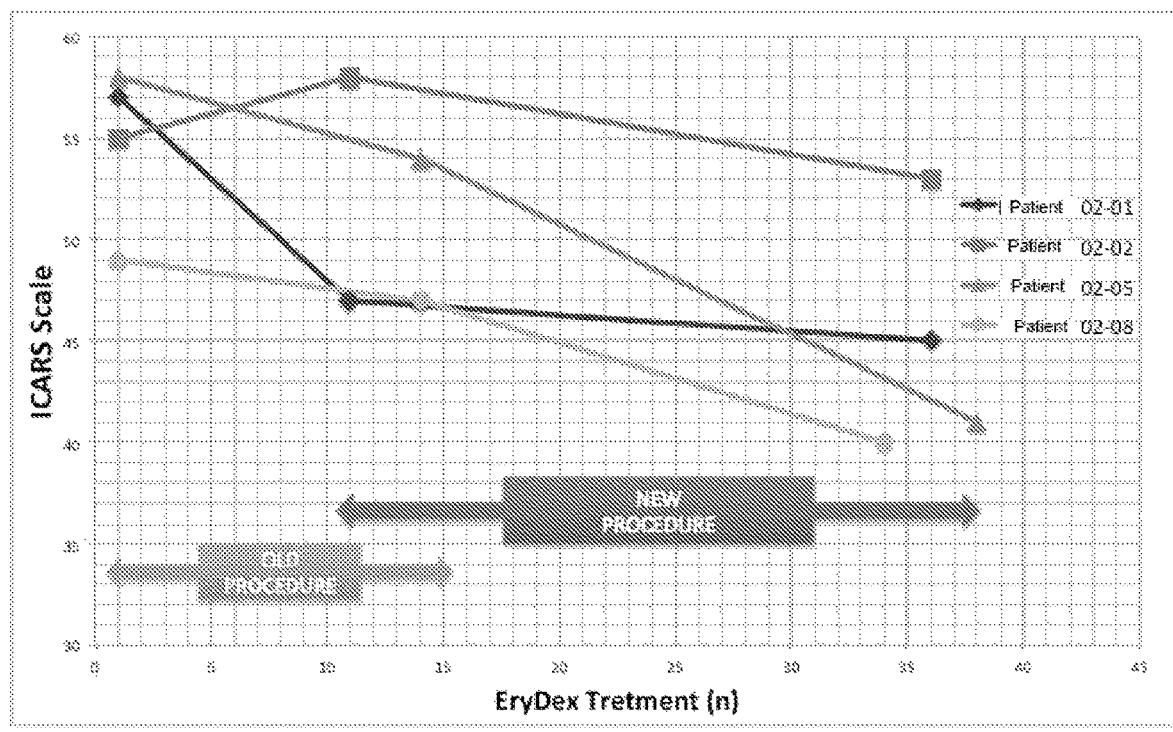
FIG. 4: the graph in figure shows the results of compassionate study on 4 patients affected from Ataxia telangiectasia (02-01, 02-02, 02,05, 02,08) treated with the erythrocytes produced by both the procedure shown in the prior art (EP0882448) (OLD Procedure) and the procedure according to the present invention (NEW Procedure).

The graph in FIG. 4 shows the ICARS values of 4 patients at the extremes of the treatment period with the OLD and NEW Procedures (in continuity with each other). The slopes of the interpolation straight lines relative to 3 out of 4 patients (Patients 02-02, 02-05, 02-08) are evidently greater during the treatment period with the NEW Procedures. The greater slope clearly indicates that in the period of use of the NEW procedures the patient improves his neurological status faster than the period of treatment with the OLD Procedures (whew in one case a patient, the 02-02, presents an even worsening). Only in one patient (02-01) improvement has a lower speed when using the NEW procedures; however, this patient had already achieved a very significant improvement with the previous treatment and, however, has improved his neurological status further with the NEW procedures.

The progressive improvement in neurological status, even in patients who responded not much or nothing to the EryDex treatment obtained with the OLD procedures, associated with a high level of tolerability of treatment, demonstrates the significant clinical benefits that the EryDex therapy obtained according to the new procedure and according to the present invention, brings to patients suffering from ataxia telangiectasia.

The invention claimed is:

1. A process for preparing erythrocytes loaded with one or more substances of pharmaceutical interest comprising the following steps:
   (A) preparing intact erythrocytes for permeabilization and loading with one or more substances of pharmaceutical interest, said preparing comprising:
      (a) swelling intact erythrocytes using a first hypotonic solution, wherein said first hypotonic solution brings the intact erythrocytes to an osmolality between 250-200 mOsm/Kg and prepares the intact erythrocytes for further swelling;
      (b) further swelling the intact erythrocytes obtained in step (a), without reaching lysis, using a second hypotonic solution more hypotonic than the first hypotonic solution, wherein said second hypotonic solution brings the intact erythrocytes to an osmolality between 200 and 170 mOsm/Kg; and
      (c) concentrating the intact erythrocytes obtained in step (b) to provide concentrated, intact erythrocytes prepared for permeabilization and loading with the one or more substances of pharmaceutical interest;
   (B) concurrently (i) permeabilizing the concentrated, intact erythrocytes of step (c) and (ii) diffusing one or more substances of pharmaceutical interest into the erythrocytes thus permeabilized by placing the concentrated, intact erythrocytes obtained in step (c) in contact with a lysing solution comprising the one or more substances of pharmaceutical interest; and subsequently
   (C) adding a sealing solution to seal the one or more substances of pharmaceutical interest within the erythrocytes.

2. The process according to claim 1, which comprises between steps (a) and (b), an additional step wherein at least part of the first hypotonic solution is removed before the addition of the second hypotonic solution.

3. The process according to claim 1, wherein said concentration step (c) is carried out by hemofiltration, haemodialysis or centrifugation of the intact erythrocytes obtained in step (b).

4. The process according to claim 1 wherein the lysing solution in step (B) brings the erythrocytes to an osmolality between 150 and 110 mOsm/Kg.

5. The process according to claim 1, wherein the sealing solution in step (C) is a hypertonic solution from 300 to 5000 mOsm/kg.

6. The process according to claim 1, said one or more substances of pharmaceutical interest are selected from the group consisting of: peptides, oligopeptides, polypeptides, proteins, oligonucleotides, nucleotide analogues, nucleosides, nucleoside analogues, hormones, immunosuppressant drugs, anti-tumor drugs, corticosteroids, glucocorticoids, anti-retroviral anti-inflammatory drugs, cytokines, toxins, substances with immunization activities, contrast media for diagnosis, particles, and nanoparticles.

7. The process according to claim 1, wherein said one or more substances of pharmaceutical interest are selected from the group consisting of: 6-mercaptopurine, fludarabine phosphate, azidothymidine phosphate, dideoxycytidine, deoxyadenosine, glutathione, bisphosphonates, prednisolone, prednisolone phosphate, dexamethasone, dexamethasone phosphate, betamethasone, betamethasone phosphate, deflazacort, thymidine phosphorylase, phenylalanine ammonia lyase, and indocyanine green.

8. The process according to claim 6, wherein said nanoparticles are selected from the group consisting of: metal-containing nanoparticles, magnetic nanoparticles, and complex nanoparticle-active molecules.

9. The process according to claim 6, wherein said particles comprise super-paramagnetic particles (SPIO).

10. The process according to claim 3, wherein said hemofiltration obtains a concentration of erythrocytes (hematocrit) above 30%.

11. The process according to claim 1, wherein step (a) is carried out maintaining the erythrocytes at a concentration (hematocrit) of 3-7%.

12. The process according to claim 1, wherein step (B) is carried out maintaining the erythrocytes at a concentration (hematocrit) of 30-65% in contact with the lysis solution containing the one or more substances of pharmaceutical interest.

13. The process according to claim 1, wherein step (C) is carried out maintaining the erythrocytes at a concentration (hematocrit) of 15-40%.

14. The process according to claim 1, wherein the erythrocytes having the one or more substances of pharmaceutical interest have an average percentage of phosphatidylserine exposure below 10% as measured with an annexin V assay.

15. The process according to claim 1, wherein the erythrocytes having the one or more substances of pharmaceutical interest have an average amount of lactate produced for every $10^6$ erythrocytes of greater than 0.100 nmol/h.

* * * * *